United States Patent [19]

Sturges

[11] Patent Number: 4,779,297
[45] Date of Patent: Oct. 25, 1988

[54] CUSHION SUPPORT ARTICLE

[76] Inventor: Doris Sturges, 514 Riverside Avenue, Lyndhurst, N.J. 07071

[21] Appl. No.: 882,756

[22] Filed: Jul. 7, 1986

[51] Int. Cl.$^4$ .................. A47G 9/00; A47C 20/00
[52] U.S. Cl. ........................... 5/468; 5/435; 5/440
[58] Field of Search .............. 5/434, 435, 436, 437, 5/443, 440, 468, 469, 431, 432; 297/180, 453; 128/149

[56] References Cited

U.S. PATENT DOCUMENTS

| | | | |
|---|---|---|---|
| D. 229,266 | 11/1973 | Zacharias | 5/434 |
| 1,986,697 | 1/1935 | Wilson . | |
| 2,085,296 | 6/1937 | Carey . | |
| 2,305,289 | 12/1942 | Coburg . | |
| 2,521,530 | 9/1950 | McGuffage | 5/431 |
| 2,551,727 | 5/1951 | Costello | 5/440 |
| 3,606,886 | 9/1971 | Bittner . | |
| 3,757,366 | 9/1973 | Sacher | 5/469 |
| 3,926,181 | 12/1975 | Eischmen | 5/436 |
| 4,206,524 | 6/1980 | Cook | 5/468 |
| 4,531,247 | 7/1985 | Eary | 5/436 |

FOREIGN PATENT DOCUMENTS 261511 11/1926 United Kingdom .................. 5/441

Primary Examiner—Alexander Grosz

[57] ABSTRACT

A cushion support article suitable for interposition between a portion of a patient's body and the patient's resting surface therefor, comprising a cushion support member having a central aperture, a cushion superposed on the top of the cushion support member, the cushion having a central aperture adapted for substantial registry with the central aperture in the cushion support member, and means to elevate the cushion support member above the resting surface of the patient to define air ventilation channels beneath the cushion support member to provide air communication with the central aperture of the cushion above which the patient rests places that portion of the body being treated. In a preferred embodiment the cushion support article comprises a cushion and means to elevate the cushion, the cushion comprising an annular base member and a bulbous deformable sheathing, the cavity therebetween being filled with a resilient material.

22 Claims, 2 Drawing Sheets

CUSHION SUPPORT ARTICLE

FIELD OF INVENTION

The present invention concerns an article for placement beneath a portion of the body of an invalid. More specifically, it concerns a cushion support article for bedridden or otherwise substantially nonambulatory individuals, who are prone, in view of such restriction in movement, to develop bed sored caused a by chafing or pressure. Most specifically, the present invention relates to a cushion support article adapted to relieve pressure from an area of the body afflicted with bed sores, and to allow air to reach the afflicted area to hasten healing.

BACKGROUND OF INVENTION

Treatment of bed sores generally takes the form of relieving pressure by placing a pillow or other soft support beneath the afflicted area. In some cases water beds are used to reduce pressure and chafing. U.S. Pat. No. 2,085,296 to Carey discloses an invalid cushion comprising an envelope and a pad or filler. The envelope is in the form of a sheet having an interior compartment formed from the plys of the sheet and which defines a central aperture, there being substantial margins to the sheet that are to lie flat on the bed or other resting surface of the individual being treated. Access to the interior compartment formed between the plys of the sheet is through a continuous circumferential slit in the central aperture, the slit being defined by the interior edges of the upper ply and the lower ply. Closure of the slit is by means of a zipper fastener. The pad similarly has a central aperture, and once the pad is inserted into the compartment in the sheet, the zipper can be closed. Although the Carey device traps air below the bed sore affected area, air does not pass through the cushion because the pad as well as the margins of the sheet rest directly on the bedding surface.

U.S. Pat. No. 1,986,697 to Wilson discloses an air ring for bedridden patients comprising an inflatable cushion having a central aperture. The cushion, which rests directly on the bed, has a tubular body forming a substantially closed circle, the terminal ends of the tubular body being relatively small, separately inflatable compartments, these compartments being provided with straps to connect one terminal compartments to another. By uncoupling the straps the Wilson device allows treatment of the patient without removal of the patient from the air ring.

U.S. Pat. Nos. 3,606,886 to Bittner and 2,305,289 to Coburg are also of interest. Bittner discloses a pressure relief cushion for corns, while Coburg discloses a surgical applicance attachable to the body of a patient to prevent bodily fluids from entering the surrounding parts of the body during surgery.

None of the prior art devices disclose a device for bedridden patients that allows free passage of air to reach the bed sore afflicted area of the patient.

Accordingly, it is an object of the present invention to provide a cushion support article to relieve pressure from a portion of a patient's body so as to prevent bed sores.

It is also an object of the present invention to provide a cushion support article to facilitate the healing of bed sores.

It is a primary object of the present invention to provide a cushion support article that allows air to reach the bed sore afflicted area of the patient.

Another object of this invention is to provide an article that can be maintained in sanitary condition.

These and other objects and advantages of the present invention are described in detail in this specification and with reference to the accompanying drawings. A summary of the invention appears immediately below.

SUMMARY OF INVENTION

In one embodiment of the present invention, the cushion support article, which is intended for placement between the afflicted area of the patient's body and the patient's resting surface, comprises a planar cushion support member having a central aperture, a cushion superposed on the cushion support member, said cushion having a central aperture adapted for substantial registry with the cushion support member aperture, and means to elevate the cushion support member above the resting surface of the patient, said means to elevate the cushion support member defining air ventilation channels beneath the cushion support member that communicate with the central aperture of the cushion support article.

In another embodiment, the cushion support article comprises a cushion having a central aperture and means to elevate the cushion above the resting surface of the patient, said cushion comprising an annular base, a bulbous elastic sheathing affixed at its terminal ends to the interior and exterior edges of the annular base forming above the base a cavity between the sheathing and the base, and resilient filler material provided within said cavity.

The preferred means for elevating the cushion or cushion support member, as the case may be, is a plurality of ribs depending below the annular base or the cushion support member, respectively. A lower base member may be provided below the elevating means, said lower base member providing stable support for the cushion support article on the resting surface of the patient. In yet another aspect of the invention, means to force circulate air through the ventilation channels and the central aperture, and, hence, to the afflicted area of the patient, is provided.

DETAILED DESCRIPTION OF THE PREFERRED EMBODIMENT

Figure 1:
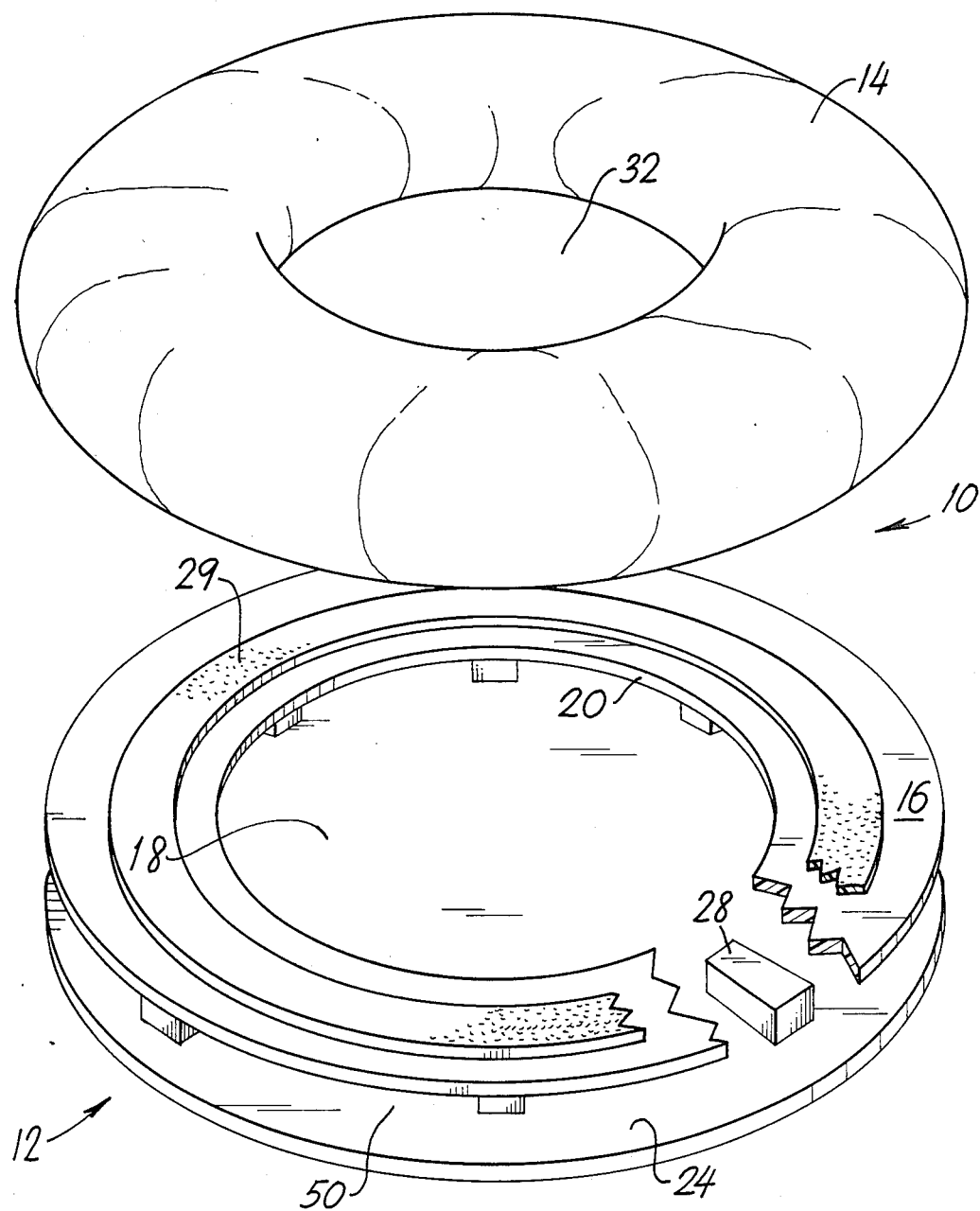
FIG. 1 is an exploded partially broken away perspective view of one embodiment of the cushion support article of the present invention.

Referring to FIG. 1, the cushion support article 10 of the present invention is seen to comprise a cushion support member, designated generally by numeral 12, and a cushion 14, the cushion 14 being superposed on the cushion support member 12.

The cushion support member 12 includes a first planar or annular base member 16 having central aperture 18 defined by edge 20 of the member 16, and optionally a second planar or lower base member 24 in spaced apart relationship to the first planar member 16 by spacer means, here shown as a plurality of radial ribs 28. The lower base member 24 is preferred in that it provides greater stability when the cushion support article 10 is placed on a resilient surface, for example, a mattress. However, spacer means may be provided that are adapted to provide a stable relationship of the article 10 to its resting surface, for example, by providing protruding flanges that increase the bottom surfaces area of the spacer means. In some instances, spacer means such as the ribs 28 shown in FIG. 1 may be sufficient in the absence of a lower base member 24, for example, where the resting surface for the afflicted portion of the patient's body is nonresilient.

The radial ribs 28 define air ventilation channels 50, which allow air to be in contact with that portion of the patient's body overlying the aperture 32 in the cushion 14, as hereinafter described.

While radial ribs 28 are preferred, the spacer means may be of any desired shape, provided sufficient void space remains between the spacer means to permit the passage of air through the air ventilation channels. For example, a plurality of cylindical pegs may be dependingly positioned uniformly from the bottom surface of the annular base member 16.

Typically, three to six radial ribs 28 would be used, depending on the size and shape of the article 10.

Preferably, the cushion support member 12 is of integral construction, and may be made from any convenient material, for example, wood, metal, and polymeric materials, for instance, thermoplastics such as polyacrylic, polystyrene and the like. Most preferably, the annular base member 16, the lower base member 24, and the radial ribs 28 are of a plastic material to permit extrusion and/or molding fabrication. Any suitable means may be used to integrally connect the planar members 16, 24 to the radial ribs 28 and would depend upon the materials of construction.

The cushion 14 has a large central aperture 32 and when in superposition with the cushion support member 12, conforms generally to the latter's geometry. Similarly, the apertures 18, 32 are sized as to provide substantial registry thereof. As shown in FIG. 1, the cushion is in the shape of a torus.

Figure 2:
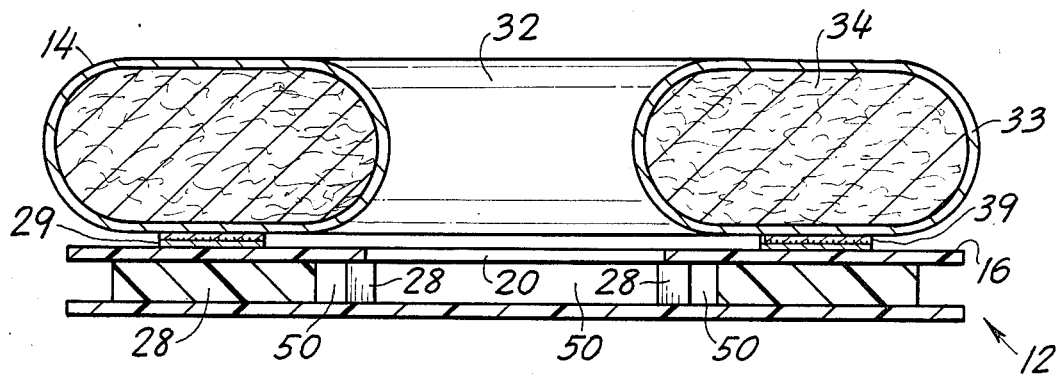
FIG. 2 is a cross-sectional view of the assembled device of FIG. 1, through the latitudinal centerline thereof.

Referring to FIG. 2, the cushion 14 has a body 33 containing a filler material 34. The cushion body 33 is in the form of a laminar sheathing and is made of a resilient material, e.g., fabric plastic, etc. Any resilient filler material can be used, for example, down, foam rubber, and synthetic cellular plastics. With suitable construction, air or other fluid could be used as a filler material. The cushion 14 may be detachably mounted to the cushion support member 12. Such mounting may be by any suitable means, for example by straps, snaps or buttons. As shown in FIG. 2 complementary reticulated nylon (e.g., Velcro TM) strips 29, 39 are provided affixed to the top of the annular base member 16 and on the cushion 14, respectively.

Preferably, the sheathing 33 is an inert, resilient plastic material, for example, a vinyl polmer, and the cushion 14 is affixedly attached to the cushion support member 12. Suitable attachment means may include adhesive, stitching, heat sealing, rivets, and the like. With such construction, a removable cushion cover is preferably employed, which cover can be removed periodically and laundered. Suitable fasteners for the cushion cover may include any conventional fastener means, for example, snaps, straps, or buttons, snaps being shown in FIG. 3 with respect to the cushion support article 100.

Figure 3:
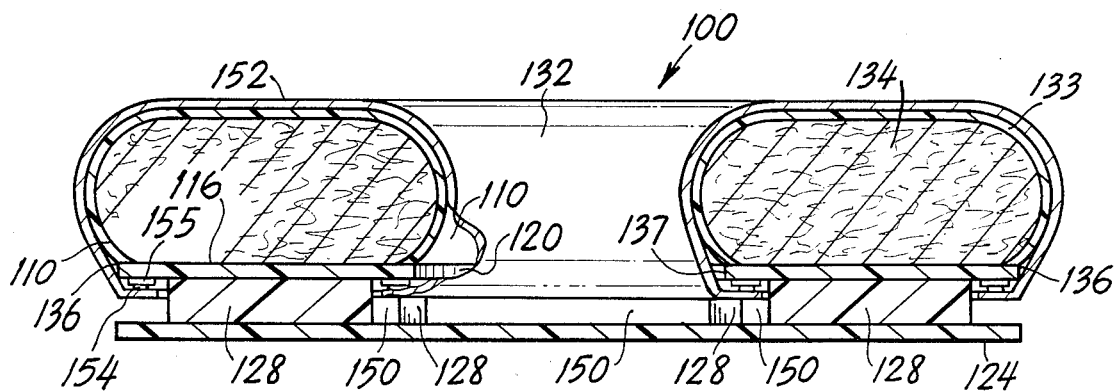
FIG. 3 is a latitudinal cross-sectional view of the preferred embodiment of the present invention.

FIG. 3 is a cross-sectional view of an alternate embodiment 100 of the cushion support article of the present invention. The cushion support article 100 comprises a cushion 110 having a central aperture 132, a lower base 124, and spacer means, shown in FIG. 3 as a plurality of radial ribs 128. The cushion comprises an annular base 116, a bulbous elastic sheathing 133, and resilient filler material 134.

Preferably, the annular base 116 and the elastic sheathing 133 are plastic materials capable of being heat sealed. The elastic sheathing may, for example, be a resilient vinyl material, which is easily sanitized and is inert to liquid spills. The sheathing 133 is affixed at the exterior circumferential edge 136 and at the interior circumferential edge 137 of the annular base member 116, by conventional means including adhesive and the aforementioned heat sealing.

Optionally, a removable annular cushion cover 152 may be provided, which cover can be periodically removed for laundering. The cover 152 is used for the comfort of the patient and would be made of a suitably soft fabric such as cotton. As shown in FIG. 3, the interior and exterior edges of the annular cushion cover 152 can be provided with a plurality of uniformly spaced apart female snap connectors 154 that are mateable with corresponding male snap connectors 155 provided on the bottom surface of the annular base 116 and proximate to its interior and exterior edges.

To use the cushion support article described herein, the patient places it beneath his or her body such that the body area afflicted by bed sores is directly above the central aperture in the cushion. Air can freely access the center of the cushion support article, in view of the air ventilation channels previously described, the air reaching the sores of the patient and aiding in the healing process. Where the lower base member 24 or 124 is not provided, the ribs would reside on the resting surface of the patient, the annular base member and said resting surface defining the air ventilation channels.

To insure that adequate air reaches the afflicted area, the air ventilation should be uniformly provided, and it is preferred that the total cross-sectional area for air passage be greater than the total cross-sectional area of the spacer means, normal to the plane of the annular base member and throughout its annular radial width. Most preferably, the cross-sectional area available for air communication defined by the ventilation channels is greater than 75% of the total annular cross-sectional area of the cushion support article.

The article 10 may come in different sizes and shapes, depending upon the location of the afflicted area and size of the patient. Typically, the article 10 is oval or circular, with a longitudinal dimension of between about 10 to 30 inches and a latitudinal dimension of between 10 to 20 inches. The height of the cushion support article is between about 1 to 6 inches, preferably about 1½ to 4 inches. The central apertures in the annular base member and in the cushion each typically represent abut 20 to 80%, preferably 40 to 75%, of the total surface area of the cushion support member and of the cushion.

In another aspect of the present invention, means to force or induce air to enter the air ventilation channels may be provided. Such means would preferably comprise a fan remotely provided and a hose or duct removably attachable within an air ventilation channel. Alternatively, a small fan provided within an air ventilation channel may be employed to convey air through the central apertures.

I claim:

1. A cushion support article for use in the treatment of bed sores, the article being interposed between a portion of a patient's body afflicted with bed sores and the patient's resting surface therefor, the cushion support article comprising a cushion having a central aperture, and spacer means, said cushion comprising an annular base member, the top surface area of the central aperture being about 40 to about 75% of the total area of the base member, a bulbous deformable sheathing affixed at its terminal ends to the interior and exterior peripheral edges of the annular base member and forming above the base member a cavity between the sheathing and the base member, and resilient filler material provided within the cavity, the spacer means projecting outwardly from the surface of the annular base member opposite the sheathing, the spacer means adapted to elevate the cushion above the resting surface of the patient, thereby defining at least one air ventilation channel beneath the cushion to provide air communication between the article's surroundings and the cushion, whereby interposition of the cushion support article beneath said portion of the patient's body allows air to pass through said ventilation channel and to said portion of the patient's body overlying the central aperture in the cushion.

2. The article of claim 1 further comprising a planar base member provided below the spacer means.

3. The article of claim 2 wherein the total cross-sectional are for air passage through the ventilation channels is greater than the total cross-sectional area of the spacer means, the cross-sectional areas being measuresd normal to the direction of air passage.

4. The article of claim 3 wherein the spacer means is a plurality of pegs.

5. The article of claim 1 wherein the spacer means is a plurality of radial ribs defining two or more air ventilation channels.

6. The article of claim 5 further comprising a planar base member provided below the spacer means.

7. The article of claim 6 wherein the total cross-sectional area for air passage through the ventilation channels is greater than the total cross-sectional area of the spacer means, the cross-sectional areas being measured normal to the direction of air passage.

8. The article of claim 1 wherein the sheathing is affixed to the annular base member by anyone of: adhesive, heat, or radio frequency sealing.

9. The article of claim 1 further comprising a removable cushion cover.

10. A cushion support article for use in the treatment of bed sores, the article being interposed between a portion of a patient's body afflicted with bed sores and the patient's resting surface therefor, the cushion support article comprising a cushion having a central aperture, spacer means, and a planar base member provided below said spacer means, said cushion comprising an annular base member, a bulbous deformable sheathing affixed at its terminal ends to the interior and exterior peripheral edges of the annular base member and forming above the base member a cavity between the sheathing and the base member, and resilient filler material provided within the cavity, the spacer means projecting outwardly from the surface of the annular base member opposite the sheathing and elevating the cushion above the resting surface of the patient, thereby defining at least one air ventilation channel beneath the cushion to provide air communication between the article's surroundings and the cushion, the cross-sectional area for air passage through the at least one ventilation channel being greater than the total cross-sectional area of the spacer means, said cross-sectional areas being measured normal to the direction of air passage, whereby interposition of the cushion support article beneath said portion of the patient's body allows air to pass through said ventilation channel and to said portion of the patient's body overlying the central aperture in the cushion.

11. The article of claim 10 wherein the spacer means is a plurality of radial ribs defining two or more ventilation channels.

12. A cushion support article for use in the treatment of bed sores, said article being interposed between a portion of a patient's body afflicted with bed sores and the patient's resting surface therefor, the cushion support article comprising a cushion support member having a first and a second planar surface; a cushion superposed on a planar surface of the cushion support member, said cushion support member and said cushion each having central apertures in substantial registry, the top surface area of the cushion aperture being at least about 94 square inches, and spacer means projecting outwardly from the planar surface of the cushion support member opposite the superposed cushion, the spacer means adapted to elevate the cushion support member above said resting surface of the patient, thereby defining at least one air ventilation channel beneath the cushion support member to provide air communication between the article's surroundings and the cushion aperture, whereby interposition of the cushion support article beneath said portion of the patient's body allows air to pass through said ventilation channel and to said portion of the patient's body overlying the central aperture in the cushion.

13. The cushion support article of claim 12 wherein the top surface area of the cushion aperture is between about 94 to about 565 square inches.

14. The article of claim 13 wherein the top surface area of the cushion aperture is about 20 to 75% of the total area of the cushion, and wherein the area of the cushion support member aperture is about 20 to 75% of the total area of the support member.

15. The article of claim 13 further comprising a planar base member provided below the spacer means.

16. The article of claim 15 wherein the total cross-sectional area for air passage through the ventilation channels is greater than the total cross-sectional area of the spacer means, the cross-sectional areas being measured normal to the direction of air passage.

17. The article of claim 15 wherein the total cross-sectional area for air passage through the ventilation channels is more than about 75% of the total cross-sectional area of the spacer means, the cross-sectional areas being measured normal to the direction of air passage.

18. The article of claim 17 wherein the spacer means is a plurality of pegs.

19. The article of claim 15 wherein the spacer means is a plurality of radial ribs defining two or more air ventilation channels.

20. The article of claim 19 wherein the total cross-sectional area for air passage through the ventilation channels is greater than the total cross-sectional areas of the radial ribs, the cross-sectional areas being measured normal to the direction of air passage.

21. The article of claim 19 wherein the total cross-sectional area for air passage through the ventilation channels is more than about 75% of the total cross-sectional areas of the radial ribs, the cross-sectional areas being measured normal to the direction of air passage.

22. The article of claim 13 wherein the cushion is integrally connected to the cushion support member.

* * * * *